United States Patent [19]
Bonnet et al.

[11] Patent Number: 6,002,006
[45] Date of Patent: Dec. 14, 1999

[54] 1(2H) QUINOLINE CARBOXYLIC ACID DERIVATIVES, METHOD FOR PREPARING SAME, AND USE THEREOF FOR SYNTHESIZING SUBSTANCES HAVING ANTIBIOTIC PROPERTIES

[75] Inventors: Alain Bonnet, Meaux; Raphael Bouchet, Pantin; Daniel Guilmard, Roissy en Brie; Alain Mazurie, Vaujours, all of France

[73] Assignee: Hoechst Marion Roussel, France

[21] Appl. No.: 09/125,537

[22] PCT Filed: Feb. 27, 1997

[86] PCT No.: PCT/FR97/00352

§ 371 Date: Sep. 28, 1998

§ 102(e) Date: Sep. 28, 1998

[87] PCT Pub. No.: WO97/31926

PCT Pub. Date: Sep. 4, 1997

[30] Foreign Application Priority Data

Feb. 28, 1996 [FR] France ................... 96 02473

[51] Int. Cl.⁶ ............... C07F 9/60; C07F 9/6558; C07D 215/14; C07D 405/06
[52] U.S. Cl. .................................. 546/23; 546/21
[58] Field of Search .......................... 546/21, 23

[56] References Cited

FOREIGN PATENT DOCUMENTS 0676409  10/1995  European Pat. Off. .

OTHER PUBLICATIONS

Kin–ya Akiba et al. Tetrahedron Letters, vol.23, No. 16, pp.–1709–1712, 1982.
Akiba et al, "Regioselective . . . –2–Phosphonates", Tetrahedron Letters vol. 23, No. 16, pp. 1709–1712, 1982, XP 000611889.
Akiba et al. "Quinolinephosphonate Derivatives", Chemical Abstracts, vol. 106, No. 13, Mar. 30, 1987, p. 684 XP 002018371.

*Primary Examiner*—Alan L. Rotman
*Attorney, Agent, or Firm*—Bierman, Muserlian and Lucas

[57] ABSTRACT

A compound of the formula

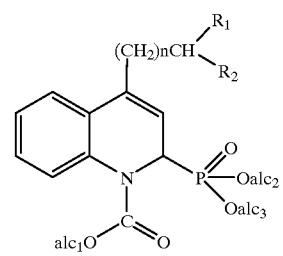

I wherein $alc_1$, $alc_2$ and $alc_3$ are alkyl of up to 8 carbon atoms, n is an integer from 0 to 8, $R_1$ and $R_2$ are O-alkyl of up to 8 carbon atoms, or form together with the carbon atom to which they are linked a cyclic acetal which are useful intermediates to produce the compounds of the formula

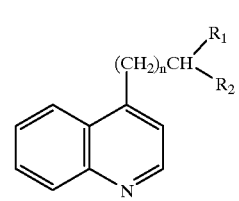

IV

8 Claims, No Drawings

1(2H) QUINOLINE CARBOXYLIC ACID DERIVATIVES, METHOD FOR PREPARING SAME, AND USE THEREOF FOR SYNTHESIZING SUBSTANCES HAVING ANTIBIOTIC PROPERTIES

CROSS-REFERENCE

This application is a 5371 of PCT/PR97/00352 filed Feb. 27, 1997.

The present invention relates to new derivatives of 1(2H) quinoline carboxylic acid, their preparation process and their use for the synthesis of products endowed with antibiotic properties.

A subject of the invention is the compounds of formula (I):

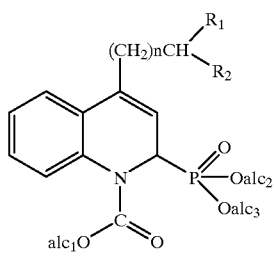

(I)

in which $alc_1$, $alc_2$ and $alc_3$ identical to or different from each other represent an alkyl radical containing up to 8 carbon atoms, n represents an integer which can vary from 0 to 8, $R_1$ and $R_2$ represent an O-alkyl radical containing up to 8 carbon atoms, or form together with the carbon atom to which they are linked a cyclic acetal.

The alkyl radical is preferably a methyl, ethyl, n-propyl, isopropyl, butyl, isobutyl or terbutyl radical.

When $R_1$ and $R_2$ form with the carbon atom to which they are linked a cyclic acetal, it is preferably a:

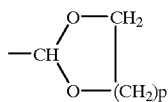

group in which p represents the number 1, 2, 3 or 4.

A quite particular subject of the invention is the compounds of formula (I) in which n represents the number 2, as well as those in which $alc_1$, $alc_2$ and $alc_3$ represent an ethyl radical.

Among the preferred compounds of the invention there can be mentioned the compounds of formula (I) in which $R_1$ and $R_2$ form together with the carbon atom to which they are linked a 1,3-dioxolane:

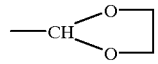

or 1,3-dioxane radical

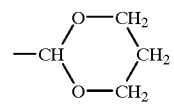

A quite particular subject of the invention is the compound of formula (I) the preparation of which is given hereafter in the experimental part.

A subject of the invention is also a preparation process for compounds of formula (I), characterized in that a compound of formula (II):

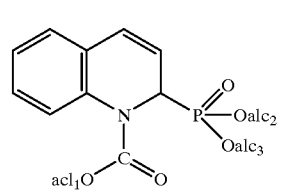

(II)

in which $alc_1$, $alc_2$ and $alc_3$ retain their previous meaning is subjected to the action of a compound of formula (III):

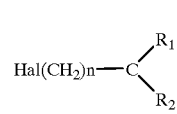

(III)

in which Hal represents a halogen atom and $R_1$, $R_2$ and n retain their previous meaning, in order to obtain the corresponding compound of formula (I).

The compounds of formula (II) used as starting products for the process of the invention can be prepared according to the processes described in Tetrah. Lett. 23(16), 1709–12 (1982) or in the Japanese Patent Application 1221–102.

In a preferred implementation of the process of the invention, Hal is a bromine or chlorine atom.

A particular subject of the invention is a process characterized in that the operation is carried out in the presence of a strong base.

The base used is butyllithium, or an alkaline or alkali earth alcoholate, for example lithium, sodium, or potassium terbutylate or teramylate or also lithium hydroxide. Sodium or potassium terbutylate or teramylate is preferably used.

Furthermore a subject of the invention is the use characterized in that a compound of formula (I) is subjected to the action of a strong base in order to obtain the corresponding compound of formula (IV):

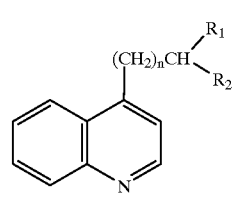

(IV)

in which n, $R_1$ and $R_2$ retain their previous meaning.

A more particular subject of the invention is the use characterized in that the strong base can be soda or preferably sodium ethylate.

The operation can also be carried out in the presence of an alkaline iodide such as sodium iodide in an aprotic polar solvent at high temperature.

Advantageously, and in particular when $R_1$ and $R_2$ form together with the carbon atom to which they are linked a cyclic acetal, the product of formula (IV) is purified in the form of the hydrochloride but it can also be in the form of the aldehyde hydrate.

A more particular subject of the invention is the use of the compound of Example 1 or 2, for the preparation of the products of formula (IV) described in the experimental part.

The compounds of formula (IV) are products known in a general fashion; they can also be prepared according to the process described in European Patent Application 676409.

The products of formula (IV) can be converted into the corresponding aldehydes:

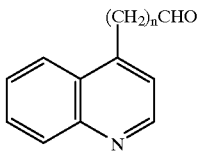

and then be converted into products having antibiotic properties according to the process described in the aforementioned Patent Application.

In this way, starting from the product of the application described in the experimental part, 11,12-dideoxy-3-de((2, 6-dideoxy-3-C-methyl-3-O-methyl-alpha-L-ribohexopyranosyl) oxy)-6-O-methyl-3-oxo-12,11-(oxycarbonyl(2-(3-(4-quinolinyl) propyl) hydrazono))-erythromycin can be prepared, which is a product having useful antibiotic properties as indicated in the aforementioned European Patent Application.

The following examples illustrate the invention without however limiting it.

EXAMPLE 1

Ethyl 2-(diethoxyphosphinyl)-4-(2-(1,3-dioxolan-2-yl) ethyl)-1(2H)-quinoline carboxylate 75 ml of a 1.6 M solution of n-butyllithium in hexane is added at −78° C., to a solution containing 33.933 g of ethyl 2-(diethoxyphosphinyl-1(2H)-quinoline carboxylate in 500 ml of tetrahydrofuran. Next 18 ml of 2-(2-bromoethyl)-1,3-dioxolane is added. The reaction medium is allowed to return to ambient temperature, then maintained under agitation for 5 hours. 300 ml of water is added, followed by agitation and decanting. The organic phase is washed with water and dried followed by filtration and elimination of the solvent. 63.45 g of product is obtained which is purified by chromatography eluting with ethyl acetate. In this way the sought product is obtained.

Rf=0.16. Yield 62.7%. NMR CDCl$_3$ ppm; 0.97 (t), CH$_3$ of N-COOEt; 1.18 (t) −1.33 (t), the CH$_3$'s of P-OEt; 1.91 (m) (2H), CH—CH$_2$—CH$_2$; 2.60 (m) (2H), =C—CH$_2$—CH$_2$; ~3.70 to 4.40 (~11H), the CH$_2$'s of P-OEt and COOEt, the O—CH$_2$'s of the ketal; 4.96 (t) (1H), O—CH—CH$_2$; 5.52 (wd) (1H), P—CH—N; 5.90 (wt), H$_3$; 7.11 (m) (1H), 7.20 to 7.35 (m) (2H).

APPLICATION 1

4-(2-(1,3-dioxolan-2-yl) ethyl-quinoline

A mixture containing 63.45 g of the product prepared in Example 1, 430 ml of a solution of 2N soda and 430 ml of absolute ethanol is heated under reflux for one hour under nitrogen.

The ethanol is eliminated and extraction is carried out with isopropyl ether. The organic phases are washed with water, dried and filtered. (Yield=43%). The solvent is distilled off and 11.263 g of product is obtained which is purified by chromatography on silica eluting with a 70-30 ethyl acetate-cyclohexane mixture. The sought product is obtained. Rf=0.4.

NMR CDCl$_3$ ppm 2.13 (m), central —CH$_2$—; 3.22 (m), =C—CH$_2$—CH$_2$; 3.86to 4.11 (m), —O—CH$_2$—CH$_2$—O—; 5.00 (t), O—CH (ketal); 7.27 (d,j=4.5) H$_3$; 8.81 (d,j=4.5) H$_2$; 7.57 (dt) and 7.71 (dt), H$_6$ and H$_7$; 8.10 (m, 2H), H$_5$ and H$_8$.

EXAMPLE 2

Ethyl 2-(diethoxyphosphinyl) 4-(2-(1,3-dioxan-2-yl) ethyl) 1(2H)-quinoline carboxylate 3.6 g of potassium terbutylate is added at 20±2° C., to a solution containing 9 g of ethyl 2-(diethoxyphosphinyl) 1(2H)-quinoline carboxylate and 45 ml of dimethylformamide. The reaction medium is maintained under agitation for 30 minutes. 9.7 g of 2-(2-iodoethyl) 1,3-dioxane is then introduced at −20°±2° C. 54 ml of water is added, the solution obtained is poured into 180 ml of water, extraction is carried out with isopropyl ether followed by washing with water, drying and washing again with isopropyl ether. The extracts are concentrated under reduced pressure in order to obtain 12 g of sought product.

APPLICATION 2

4-(2-(1,3-dioxan-2-yl) ethyl quinoline hydrochloride.

7.5 g of sodium ethylate is introduced at +20°±2° C., into a solution containing 10 g of the product prepared in Example 1 or 2 and 50 ml of ethanol 100. The mixture obtained is taken to reflux for 1 hour followed by cooling down to 20°±2° C. then agitation is maintained for 1 hour and 30 minutes. Distillation under reduced pressure is carried out and then 50 ml of water is added at 20°±2° C. Extraction is carried out with isopropyl ether followed by washing with water, drying over sodium sulphate, separation and washing with isopropyl ether. Concentration is carried out and 3.89 g of sought product is obtained in the form of a base. 3.76 g of the product obtained is put into solution at 20° C. in 19 ml of ethyl acetate, 7.6 ml of a solution of ethyl acetate with 10% hydrochloric acid is added over 20 minutes, the reaction medium is maintained under agitation for 1 hour, filtered, the precipitate is washed with ethyl acetate, dried at 40° C. for 2 hours and 2.56 g of the expected hydrochloride is obtained.

We claim:

1. A compound of the formula

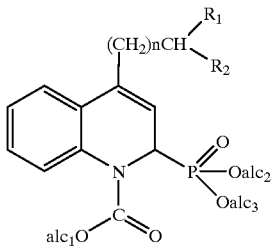

wherein $alc_1$, $alc_2$ and $alc_3$ are alkyl of up to 8 carbon atoms, n is an integer from 0 to 8, $R_1$ and $R_2$ are O-alkyl of up to 8 carbon atoms, or form together with the carbon atom to which they are linked a cyclic acetal.

2. A compound of Formula I as defined in claim 1 in which $R_1$ and $R_2$ form together with the carbon atom to which they are linked

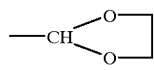

or

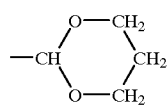

3. A compound of claim 1 which is ethyl 2-(diethoxyphosphinyl)-4-(2-(1,3-dioxolan-2-yl) ethyl)-1-(2H)-quinoline carboxylate, or ethyl 2(diethoxyphosphinyl) 4-(2-(1,3-dioxan-2-yl) ethyl) 1 (2H)-quinoline carboxylate.

4. A process for the preparation of a compound of claim 1 comprising reacting a compound of the formula

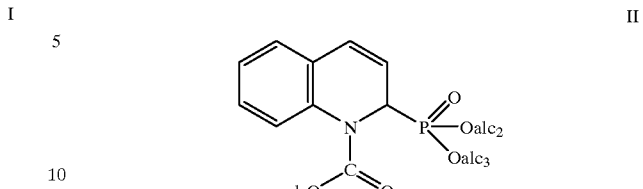

wherein $alc_1$, $alc_2$ and $alc_3$ are defined as in claim 1 with a compound of the formula

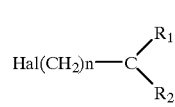

in which Hal is halogen and $R_1$, $R_2$ and n are defined as in claim 1 to obtain the corresponding compound of formula (I).

5. The process according to claim 4, characterized in that the operation is carried out in the presence of a strong base.

6. The process according to claim 5, characterized in that the base used is sodium or potassium terbutylate or teramylate.

7. A compound of claim 1 wherein n is z.

8. A compound of claim 1 wherein $alc_1$, $alc_2$ and $alc_3$ are each —$CH_2$—$CH_3$.

* * * * *